(12) United States Patent
Pappone et al.

(10) Patent No.: US 9,962,224 B2
(45) Date of Patent: *May 8, 2018

(54) IRRIGATED CATHETER WITH IMPROVED FLUID FLOW

(71) Applicant: ST. JUDE MEDICAL, ATRIAL FIBRILLATION DIVISION, INC., St. Paul, MN (US)

(72) Inventors: Carlo Pappone, Lecco (IT); Alan de la Rama, Cerritos, CA (US); Peter Chen, Irvine, CA (US); Cary Hata, Irvine, CA (US)

(73) Assignee: ST. JUDE MEDICAL, ATRIAL FIBRILLATION DIVISION, INC., St. Paul, MN (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/390,048

(22) Filed: Dec. 23, 2016

(65) Prior Publication Data

US 2017/0105796 A1    Apr. 20, 2017

Related U.S. Application Data

(63) Continuation of application No. 13/948,935, filed on Jul. 23, 2013, now Pat. No. 9,561,075, which is a
(Continued)

(51) Int. Cl.
*A61B 18/14* (2006.01)
*A61M 25/00* (2006.01)
(Continued)

(52) U.S. Cl.
CPC ....... *A61B 18/1492* (2013.01); *A61M 25/003* (2013.01); *A61M 25/007* (2013.01);
(Continued)

(58) Field of Classification Search
CPC .............. A61B 18/1492; A61B 18/18; A61B 2018/00011; A61B 2018/00101;
(Continued)

(56) References Cited

U.S. PATENT DOCUMENTS 4,325,374 A    4/1982    Komiya
5,163,905 A   11/1992    Don Michael
(Continued)

FOREIGN PATENT DOCUMENTS

WO    1996034652 A1    11/1996
WO    1999056812 A2    11/1999
(Continued)

OTHER PUBLICATIONS

"International Search Report and Written Opinion of the International Searching Authority", PCT/US2010/049836 dated Nov. 15, 2010.

*Primary Examiner* — Bhisma Mehta
*Assistant Examiner* — Brandy S Lee
(74) *Attorney, Agent, or Firm* — Armstrong Teasdale LLP

(57) ABSTRACT

An irrigated catheter with uniform cooling and/or uniform fluid distribution in longitudinally spaced apart elution holes by varying the diameter of a fluid delivery lumen. A number of elution holes are provided in a tip region of a catheter body, and these elution holes are in fluid communication with the lumen through ducts. The fluid delivery lumen may be provided with a flow constrictor to restrict flow of fluid towards the distal region.

17 Claims, 8 Drawing Sheets

Related U.S. Application Data continuation of application No. 11/696,657, filed on Apr. 4, 2007, now Pat. No. 8,517,999.

(51) Int. Cl.
*A61M 25/10* (2013.01)
*A61B 18/00* (2006.01)

(52) U.S. Cl.
CPC .... *A61M 25/0069* (2013.01); *A61M 25/0082* (2013.01); *A61M 25/1011* (2013.01); *A61B 2018/00011* (2013.01); *A61B 2018/00577* (2013.01); *A61B 2218/002* (2013.01); *A61M 2025/0073* (2013.01); *A61M 2025/1047* (2013.01)

(58) Field of Classification Search
CPC ........... A61B 2018/00214; A61B 2018/00898; A61B 2218/002; A61B 5/04; A61B 2018/00577; A61M 2025/0034; A61M 2025/0073; A61M 2025/1047; A61M 25/003; A61M 25/0069; A61M 25/007; A61M 25/0082; A61M 25/1011
See application file for complete search history.

(56) References Cited

U.S. PATENT DOCUMENTS

| | | | |
|---|---|---|---|
| 5,279,299 | A | 1/1994 | Imran |
| 5,378,230 | A | 1/1995 | Mahurkar |
| 5,462,521 | A | 10/1995 | Brucker et al. |
| 5,487,385 | A | 1/1996 | Avitall |
| 5,520,682 | A | 5/1996 | Baust et al. |
| 5,545,200 | A | 8/1996 | West et al. |
| 5,772,642 | A | 6/1998 | Ciamacco, Jr. et al. |
| 5,792,140 | A | 8/1998 | Tu et al. |
| 5,800,428 | A | 9/1998 | Nelson et al. |
| 5,833,632 | A | 11/1998 | Jacobsen et al. |
| 5,893,885 | A | 4/1999 | Webster, Jr. |
| 5,902,328 | A | 5/1999 | Lafontaine et al. |
| 5,919,188 | A | 7/1999 | Shearon et al. |
| 5,944,022 | A | 8/1999 | Nardella et al. |
| 5,951,471 | A | 9/1999 | De La Rama et al. |
| 5,954,719 | A | 9/1999 | Chen et al. |
| 5,992,418 | A | 11/1999 | De La Rama et al. |
| 6,001,095 | A | 12/1999 | De La Rama et al. |
| 6,010,500 | A | 1/2000 | Sherman et al. |
| 6,017,338 | A | 1/2000 | Brucker et al. |
| 6,030,382 | A | 2/2000 | Fleischman et al. |
| 6,053,912 | A | 4/2000 | Panescu et al. |
| 6,063,080 | A | 5/2000 | Nelson et al. |
| 6,080,151 | A | 6/2000 | Swartz et al. |
| 6,171,275 | B1* | 1/2001 | Webster, Jr. ....... A61B 18/1492 600/374 |
| 6,210,409 | B1 | 4/2001 | Ellman et al. |
| 6,217,573 | B1 | 4/2001 | Webster |
| 6,233,476 | B1 | 5/2001 | Strommer et al. |
| 6,235,022 | B1 | 5/2001 | Hallock et al. |
| 6,251,134 | B1 | 6/2001 | Alt et al. |
| 6,273,876 | B1 | 8/2001 | Klima et al. |
| 6,325,797 | B1 | 12/2001 | Stewart et al. |
| 6,346,104 | B2 | 2/2002 | Daly et al. |
| 6,356,790 | B1 | 3/2002 | Maguire et al. |
| 6,379,349 | B1 | 4/2002 | Mueller Gerhard et al. |
| 6,385,472 | B1 | 5/2002 | Hall et al. |
| 6,405,067 | B1 | 6/2002 | Mest et al. |
| 6,464,632 | B1 | 10/2002 | Taylor |
| 6,493,590 | B1 | 12/2002 | Wessman et al. |
| 6,498,944 | B1 | 12/2002 | Ben-Haim et al. |
| 6,604,003 | B2 | 8/2003 | Fredricks et al. |
| 6,611,699 | B2 | 8/2003 | Messing |
| 6,690,963 | B2 | 2/2004 | Ben-Haim et al. |
| 6,780,183 | B2 | 8/2004 | Jimenez et al. |
| 6,788,967 | B2 | 9/2004 | Ben-Haim et al. |
| 6,796,966 | B2 | 9/2004 | Thomas |
| 6,921,397 | B2 | 7/2005 | Corcoran et al. |
| 6,980,843 | B2 | 12/2005 | Eng et al. |
| 7,013,169 | B2 | 3/2006 | Bowe |
| 7,137,395 | B2 | 11/2006 | Fried et al. |
| 7,197,354 | B2 | 3/2007 | Sobe |
| 7,263,397 | B2 | 8/2007 | Hauck et al. |
| 7,386,339 | B2 | 6/2008 | Strommer et al. |
| 7,389,148 | B1 | 6/2008 | Morgan |
| 7,416,552 | B2 | 8/2008 | Paul et al. |
| 7,468,027 | B2 | 12/2008 | Barbut et al. |
| 7,536,218 | B2 | 5/2009 | Govari et al. |
| 7,537,596 | B2* | 5/2009 | Jensen ............... A61B 17/1655 606/270 |
| 7,565,208 | B2 | 7/2009 | Harris et al. |
| 7,615,050 | B2 | 11/2009 | Cross et al. |
| 7,669,309 | B2 | 3/2010 | Johnson et al. |
| 7,699,771 | B2 | 4/2010 | Wendlandt et al. |
| 7,706,891 | B2 | 4/2010 | Hastings et al. |
| 7,824,406 | B2 | 11/2010 | Wang et al. |
| 7,824,517 | B2 | 11/2010 | Kampa et al. |
| 7,826,881 | B1 | 11/2010 | Beatty et al. |
| 7,857,810 | B2 | 12/2010 | Wang et al. |
| 7,873,401 | B2 | 1/2011 | Shachar |
| 8,187,267 | B2 | 5/2012 | Pappone et al. |
| 9,561,075 | B2* | 2/2017 | Pappone et al. ........ A61B 18/18 604/19 |
| 2001/0012956 | A1 | 8/2001 | Behl et al. |
| 2002/0058866 | A1 | 5/2002 | Segner et al. |
| 2002/0156420 | A1 | 10/2002 | Anderson et al. |
| 2003/0125730 | A1 | 7/2003 | Berube et al. |
| 2004/0015215 | A1 | 1/2004 | Fredricks et al. |
| 2004/0034348 | A1 | 2/2004 | Rashidi |
| 2004/0153056 | A1 | 8/2004 | Muller et al. |
| 2004/0181138 | A1 | 9/2004 | Hindricks et al. |
| 2004/0204671 | A1 | 10/2004 | Stubbs et al. |
| 2004/0220461 | A1 | 11/2004 | Schwartz |
| 2004/0231683 | A1 | 11/2004 | Eng et al. |
| 2004/0236350 | A1 | 11/2004 | Lewis et al. |
| 2004/0243143 | A1 | 12/2004 | Corcoran et al. |
| 2004/0267106 | A1 | 12/2004 | Segner et al. |
| 2005/0004563 | A1 | 1/2005 | Racz et al. |
| 2005/0049583 | A1 | 3/2005 | Swanson |
| 2005/0054989 | A1 | 3/2005 | McGuckin et al. |
| 2005/0070894 | A1 | 3/2005 | McClurken |
| 2005/0096647 | A1 | 5/2005 | Steinke et al. |
| 2005/0143729 | A1 | 6/2005 | Francischelli et al. |
| 2005/0187561 | A1 | 8/2005 | Lee-Sepsick et al. |
| 2005/0197633 | A1 | 9/2005 | Schwartz et al. |
| 2005/0204671 | A1 | 9/2005 | Heuvel et al. |
| 2005/0272975 | A1 | 12/2005 | McWeeney et al. |
| 2006/0004353 | A1 | 1/2006 | Koyfman et al. |
| 2006/0009740 | A1 | 1/2006 | Higgins et al. |
| 2006/0015126 | A1 | 1/2006 | Sher |
| 2006/0064123 | A1 | 3/2006 | Bonnette et al. |
| 2006/0149192 | A1 | 7/2006 | Deniega et al. |
| 2006/0200191 | A1 | 9/2006 | Zadno Azizi |
| 2006/0265043 | A1 | 11/2006 | Mandrusov et al. |
| 2006/0287650 | A1 | 12/2006 | Cao et al. |
| 2007/0021743 | A1 | 1/2007 | Rioux et al. |
| 2007/0060847 | A1 | 3/2007 | Leo et al. |
| 2007/0073288 | A1 | 3/2007 | Hall et al. |
| 2007/0156114 | A1 | 7/2007 | Worley et al. |
| 2007/0179491 | A1 | 8/2007 | Kratoska et al. |
| 2007/0270791 | A1 | 11/2007 | Wang et al. |
| 2007/0299424 | A1 | 12/2007 | Cumming et al. |
| 2008/0091193 | A1 | 4/2008 | Kauphusman et al. |
| 2008/0091195 | A1 | 4/2008 | Sliwa et al. |
| 2008/0139999 | A1 | 6/2008 | Gibson et al. |
| 2008/0161789 | A1 | 7/2008 | Thao et al. |
| 2008/0249522 | A1 | 10/2008 | Pappone et al. |
| 2008/0275428 | A1 | 11/2008 | Tegg et al. |
| 2008/0281319 | A1 | 11/2008 | Paul et al. |
| 2008/0294158 | A1 | 11/2008 | Pappone et al. |
| 2008/0300589 | A1 | 12/2008 | Paul et al. |
| 2008/0312713 | A1 | 12/2008 | Wilfley et al. |
| 2009/0012517 | A1 | 1/2009 | De La Rama et al. |
| 2009/0018497 | A1 | 1/2009 | Birchard et al. |
| 2009/0228092 | A1 | 9/2009 | Raeder-Devens et al. |

(56) References Cited

U.S. PATENT DOCUMENTS

| | | |
|---|---|---|
| 2009/0247993 A1 | 10/2009 | Kirschenman et al. |
| 2009/0287210 A1 | 11/2009 | Kauphusman et al. |
| 2010/0004632 A1 | 1/2010 | Wu et al. |
| 2010/0174177 A1 | 7/2010 | Wu |

FOREIGN PATENT DOCUMENTS

| | | |
|---|---|---|
| WO | 2005048858 A1 | 6/2005 |
| WO | 2005094661 A1 | 10/2005 |
| WO | 2007015139 A2 | 2/2007 |
| WO | 2008010039 A2 | 1/2008 |
| WO | 2009120982 A2 | 10/2009 |

* cited by examiner

IRRIGATED CATHETER WITH IMPROVED FLUID FLOW

CROSS REFERENCE TO RELATED APPLICATIONS

This application is a Continuation of U.S. patent application Ser. No. 13/948,935 filed Jul. 23, 2013, which is a Continuation of U.S. patent application Ser. No. 11/696,657 filed Apr. 4, 2007, now U.S. Pat. No. 8,517,999, the contents of which are hereby incorporated by reference in their entireties.

FIELD OF THE INVENTION

The field of the invention is catheters.

BACKGROUND OF THE INVENTION

Ablation catheters using RF (radio frequency) energy are known. A typical ablation catheter has electrodes located at the catheter tip and delivers RF energy to ablate selected tissue areas in a patient. For example, patients with arrhythmia experience irregular heart beats caused by arrhythmogenic electrical signals generated in cardiac tissues. Such patients may be treated by ablating those cardiac tissues that generate such unintended electrical signals with RF energy. With the help of sensing and mapping tools, an electrophysiologist can determine the region of cardiac tissue targeted for ablation. Once determined, a catheter tip having one or more electrodes is positioned over the targeted tissue. Then, the user sends RF energy from the generator to the electrodes, creating sufficient heat to damage the targeted tissue. By damaging and scarring the targeted tissue, aberrant electrical signal generation or transmission is interrupted.

Application of curative energy is currently performed endocardially with the objective of reaching the epicardium to create a fully transmural lesion. This is important in all arrhythmias especially during ablation for atrial fibrillation and ventricular tachycardia. In the former case, transmural lesions are required to create conduction block to isolate relevant structures while in the latter case the arrhythmogenic substrate is located often in the epicardial layer of ventricular walls. Delivery of the energy is limited by the increase of temperature at the interface between catheter tip and endocardial surface and there is a good correlation between thrombus formation and high temperature. A temperature sensor is typically provided near the tip of the catheter so the user may monitor the operating temperature to ensure that overheating does not occur in the catheter tip and in the surrounding tissues. One known solution to prevent overheating is by having an irrigation system embedded within the catheter. In brief, a typical irrigation system includes a delivery lumen inside of the catheter body to supply cooling fluid, such a saline, from a pump to the catheter tip. An irrigation system may internally irrigate the catheter tip, where the cooling fluid circulates within the catheter tip. Another type of irrigation system delivers cooling fluid from within the catheter tip to the outside of the catheter tip which also cools the surrounding tissues. Catheters with an irrigated tip allow the delivery of more energy with a lower temperature at the tissue/catheter interface thus minimizing thrombus formation while maximizing deep lesion creation in the tissue. Despite numerous desirable properties, however, known irrigated catheters have several disadvantages. For example, because the temperature of the catheter tip region can vary depending on factors such as its proximity to an electrode and irrigation duct, it is difficult to monitor and ensure that all heated surfaces along the catheter tip are adequately cooled. Often the catheter tip is positioned not perpendicularly to the tissue but tangentially to increase the tip/tissue contact area as for example during ablation of the inferior part of the right sided pulmonary vein. In this situation and in every other situation where a tip side/tissue contact is required, a uniform cooling of the catheter tip would further reduce thrombus formation while allowing development of larger electrodes to more efficiently deliver energy for ablation. In this way the entire electrode surface can be used to ablate a pathological tissue without overheating any portion of the catheter tip and causing thrombus formation.

Thus, there is still a need for irrigated ablation catheter where the irrigation pattern is controlled to provide desired relative uniform cooling to the catheter tip and/or surrounding tissues.

All referenced patents, applications and literatures are incorporated herein by which is incorporated by reference herein is inconsistent or contrary to the definition of that term provided herein, the definition of that term provided herein applies and the definition of that term in the reference does not apply. The contemplated embodiments may seek to satisfy one or more of the above-mentioned desire. Although the present invention may obviate one or more of the above-mentioned desires, it should be understood that some aspects of the invention might not necessarily obviate them.

BRIEF DESCRIPTION OF THE INVENTION

Embodiments of catheters, systems and methods are disclosed that provide, among other things, substantially uniform cooling of ablation electrodes and/or the surrounding tissues in use. The catheter may include an elongated tubular catheter body having a distal end, a proximal end, and a lumen extending longitudinally within the catheter body. A number of elution holes may be provided in the catheter tip region, and these holes are in fluid communication with the lumen through ducts. As such, a cooling fluid may be delivered from a pump, through the lumen, through the ducts, and out of the holes to the environment outside of the catheter.

Contemplated catheters have at least one electrode positioned at the distal end, and the lumen may have varying diameters throughout so as to provide a desired fluid outflow pattern when flowing out of elution holes. Of the many contemplated patterns, it is desired that the varying lumen diameters are configured such that fluid outflow rate at all of the elution holes is substantially the same. Among the many different possibilities contemplated, the lumen may have a diameter that is smaller at a distal end than at a proximal end. Further, it is contemplated that the decrease in diameter may be defined by a tapered section in the lumen.

The ducts may be positioned at a tilted angle from the main lumen, or can be substantially perpendicular to the main lumen. In exemplary embodiments the ducts and the main lumen are formed at angles between 35 to 90 degrees, more specifically, 45 to 90 degrees, even more specifically between 80 to 90 degrees, and most preferably at substantially 90 degrees. In embodiments where the ducts are tilted, they can tilt forward and also backward.

Contemplated lumen diameters may vary from about 0.005 inches to about 0.045 inches, and the tapered section may decrease the diameter by about 5% to about 40%, when comparing the two diameters immediately adjacent the tapered section. In other embodiments, there are no such tapered sections, and the diameter gradually decreases along the distal region of the catheter.

In some embodiments of the contemplated device, the catheter may have at least six ducts at a single junction with the main lumen, and these ducts may be evenly and radially spread out, evenly angled from each other to form a complete circle of 360 degrees.

The ducts optionally have an inner surface with a surface pattern that causes the outflow of cooling fluid to form an irregular pattern upon exiting the holes. For example, the pattern is a spiral groove, so that the spraying pattern is an outwardly spraying swirl.

The catheter may also include at least one inflatable balloon. In some embodiments, the balloon may be attached to less than 60% of a circumference of a section of the catheter body, instead of completely surrounding a longitudinal section of the catheter body; or in another embodiment, the balloon may be attached to less than 52% of a circumference of a section of the catheter body.

The optional balloon can have an inflated shape such as a half-dome. Other suitable shapes can also be implemented depending on the shape and size of the body lumen and tissue area intended for treatment.

Further, the balloons can be positioned opposite to elution holes and/or electrodes so that the inflatable balloon can assist in physically pressing the electrode to the targeted tissue for ablation.

DETAILED DESCRIPTION OF THE INVENTION

The invention can now be better understood by turning to the following detailed description of numerous embodiments, which are presented as illustrated examples of the invention defined in the claims. It is expressly understood that the invention as defined by the claims may be broader than the illustrated embodiments described below.

Many alterations and modifications may be made by those having ordinary skill in the art without departing from the spirit and scope of the invention. Therefore, it must be understood that the illustrated embodiment has been set forth only for the purposes of example and that it should not be taken as limiting the invention as defined by the following claims. For example, notwithstanding the fact that the elements of a claim are set forth below in a certain combination, it must be expressly understood that the invention includes other combinations of fewer, more or different elements, which are disclosed herein even when not initially claimed in such combinations.

As used herein, the term "duct" is synonymous with "side channel", both are used herein to describe fluid delivery paths branching off of the main lumen of the catheter.

Figure 1:
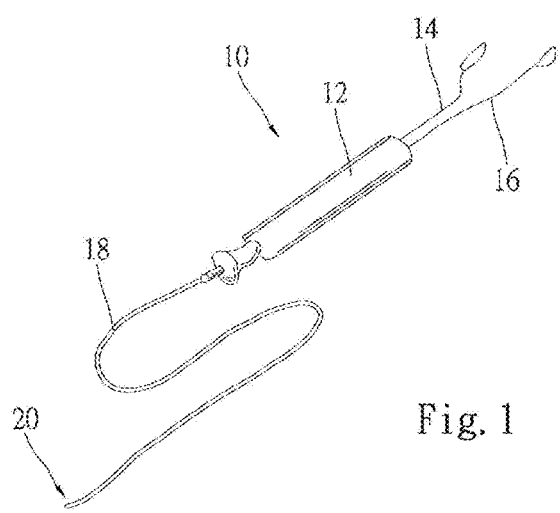
FIG. 1 is a perspective view of an irrigation catheter system according to an aspect of the inventive subject matter.

Referring now to FIG. 1, which illustrates a catheter system 10, having control unit body 12, tubing sets 14 and 16, and an elongated catheter body 18 with a distal region 20. Tubing sets 14 and 16 can be connected to any suitable known devices in the art such as, for example, a monitor/display, RF generator, signal processor, fluid pump, etc. The system 10 may also use a temperature sensor and mapping tool such as that described in U.S. Pat. No. 6,217,573.

Figure 2:
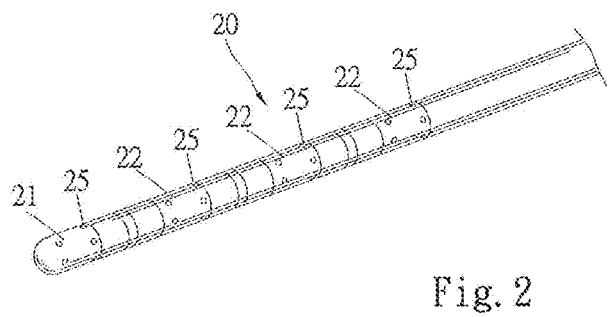
FIG. 2 is a perspective view of the catheter distal region according to an aspect of the inventive subject matter.

In FIG. 2, catheter distal region 20 has bands of electrodes 22 positioned spaced apart in different longitudinal sections. Each band of electrodes 22 has elution holes 25 located in the same longitudinal sections. At the terminal end is catheter tip 21, also having electrodes. Catheter tip 21 can be manufactured separately and attached to the rest of the elongated catheter body.

The contemplated catheter tip 21 can be made of suitable biocompatible materials to conduct RF energy and to withstand temperature extremes. Suitable materials include natural and synthetic polymers, various metals and metal alloys, naturally occurring materials, textile fibers, glass and ceramic materials, sol-gel materials, and all reasonable combinations thereof. In one embodiment, the catheter tip 21 is made of 90% platinum with 10% iridium.

Figure 3:
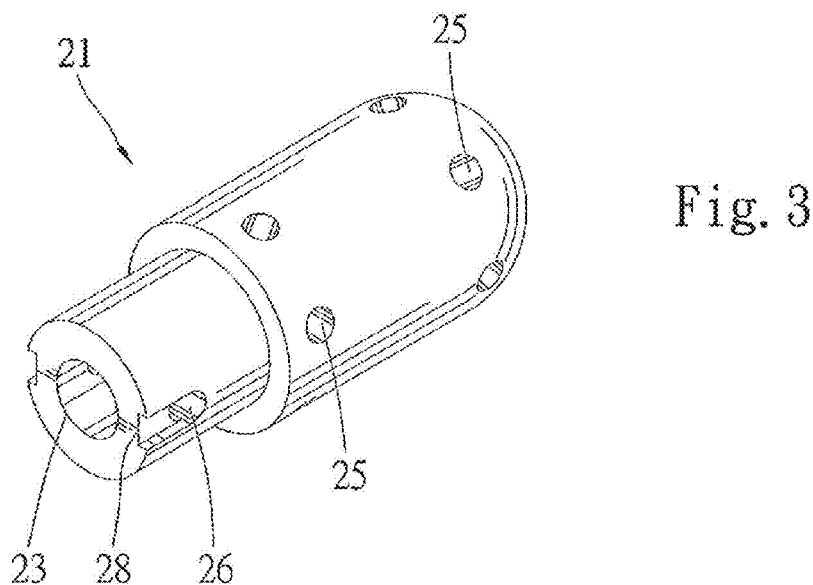
FIG. 3 is a perspective view of the catheter tip according to an aspect of the inventive subject matter.

FIG. 3 shows an exemplary embodiment of the catheter tip 21, having a through hole 26 and groove 28. Hole 26 and groove 28 are used to help attach the catheter tip 21 to the catheter body 18. Catheter body 18 has corresponding structures to matingly couple to the groove 28 and hole 26.

Figure 4:
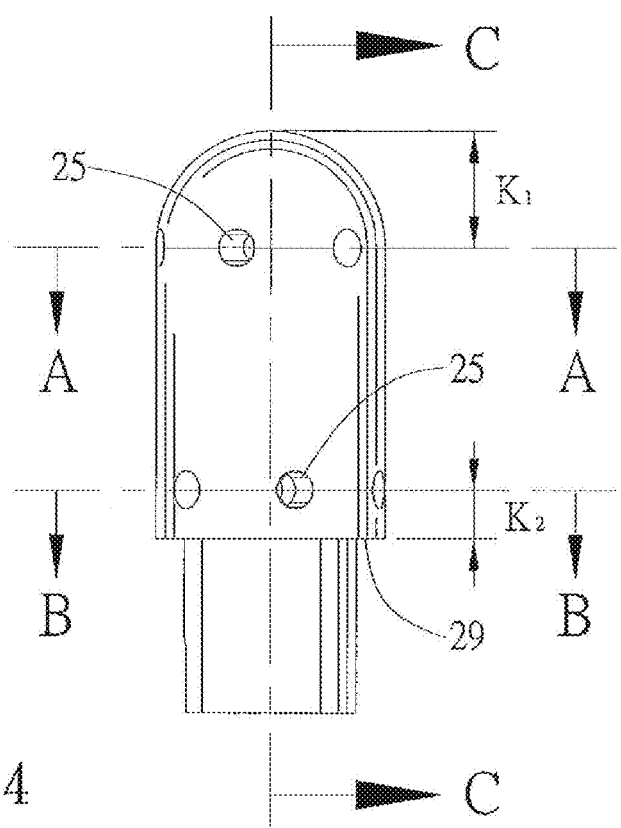
FIG. 4 is a side view of the catheter tip according to an aspect of the inventive subject matter.

FIG. 4 is a side view of the catheter tip 21. Exemplary embodiments of the catheter tip 21 have two rows of elution holes 25. In this figure, line A-A represents the first row of elution holes, and line B-B represents the second row of elution holes. The terminal end of the tip can be in any configuration, and may be spherical. The distance K1 between the most distal tip of the spherical end to the center of the first row of elution holes may be about 0.039 inches in one embodiment. The distance K2 between the edge 29 to the center of the second row of elution holes may be about 0.020 inches. The diameter of both rows of elution holes may be about 0.016 inches. As for arrangement of electrodes, mapping devices and sensors, these can be referenced from known ablation catheters such as U.S. Pat. No. 6,611,699.

Figures 4A, 4B:
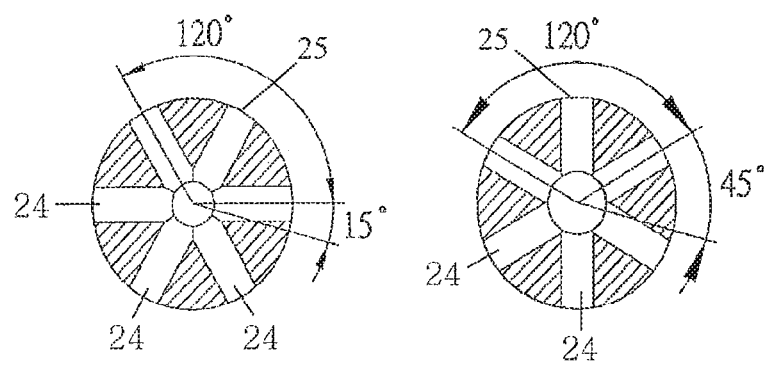
FIG. 4A is a cross sectional view of the catheter tip of FIG. 4 at line A-A, according to an aspect of the inventive subject matter.
FIG. 4B is a cross sectional view of the catheter tip of FIG. 4 at line B-B, according to an aspect of the inventive subject matter.

The number and configuration of elution holes 25 depends on the intended use of the catheter. For example, FIG. 4 shows a configuration where six elution holes 25 are provided in each of the two rows. Each elution hole 25 is fluidly connected with main lumen 23 via ducts 24. Referring to FIGS. 4A and 4B, this configuration provides six ducts 24 radially spread out and spaced evenly from each other in substantially the same degree of angle. This configuration allows all around irrigation and cooling. In comparing FIGS. 4A and 4B, the two rows of elution holes are offset by about 30 degrees. By doing so, the offset rows of elution holes provide more evenly distributed irrigation. It is also contemplated that these two rows may be offset by between 15-45 degrees, or more specifically, by about 30 degrees.

Figure 5:
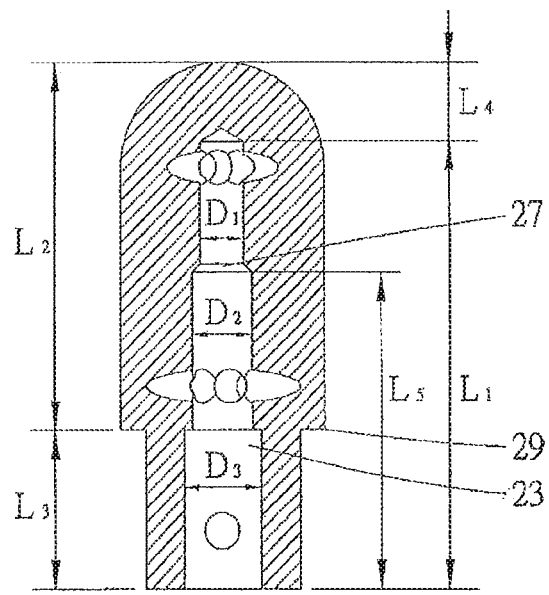
FIG. 5 is a longitudinal cross sectional view of the catheter tip of FIG. 4 at line C-C, according to an aspect of the inventive subject matter.

FIG. 5 provides exemplary dimensions of the various elements in the catheter tip 21. In one embodiment, the diameter D1 of the distal portion of the main lumen may be about 0.019 inches, and the proximal portion of the lumen, after the tapered flow constrictor 27, may have a diameter D2 of about 0.028 inches. The diameter D3 of the main lumen at the neck portion of the catheter tip 21 may be about 0.034 inches. In other embodiments, the diameter of the main lumen may range from about 0.005 inches to about 0.045 inches, and the tapered section may decrease the diameter by about 5% to about 40% comparing the two diameters immediately adjacent the tapered section.

The terminal end of the main lumen may end in a flat cone shape, and the distance L1 from the edge of the flat cone to the proximal end of the neck portion may be about 0.194 inches. The distance L2 from the tip of the spherical end to the edge 29 may be about 0.158 inches. The distance L3 of the neck from the end of the neck to the edge 29 may be about 0.065 inches. The distance L4 from the edge of the flat cone to the terminal tip of the sphere may be about 0.030 inches. Distance L5 is measured from the larger edge of the tapered flow constrictor 27 to the end of neck, and it may be about 0.135 inches.

Figure 6:
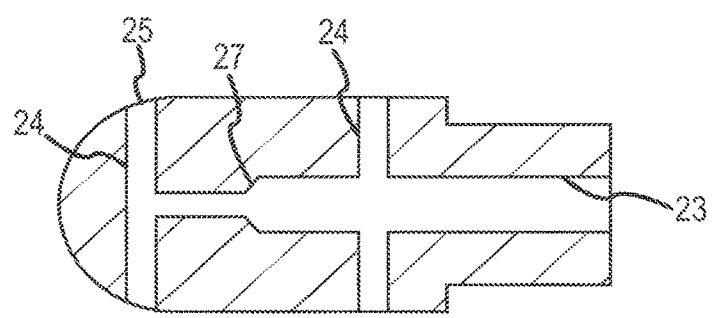
FIG. 6 is a longitudinal cross section view of a catheter tip illustrating varied lumen diameter, according to an aspect of the inventive subject matter.
Figure 7:
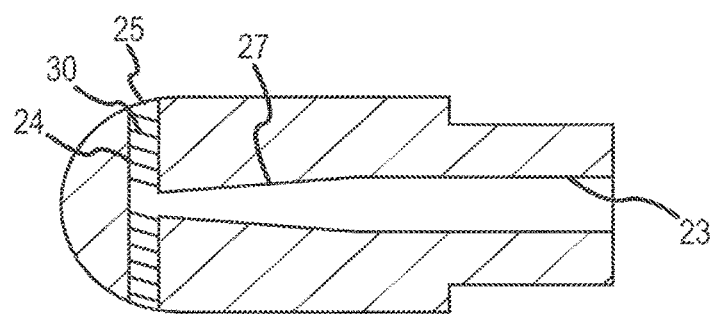
FIG. 7 is a longitudinal cross section view of a catheter tip illustrating varied lumen diameter, according to an aspect of the inventive subject matter.

FIGS. 6 and 7 illustrate different possible configurations of the flow constrictor 27. The flow constrictor 27 limits or constricts the volume of fluid as the fluid passes toward the distal end of the catheter tip. By decreasing the main lumen 23 diameter using a flow constrictor 27 located substantially equidistant from the first row and from the second row, as shown in FIG. 6, the volume of fluid reaching the first row of elution holes 25 is effectively decreased, causing fluid output in the first row of elution holes 25 to be substantially the same volume as the fluid output in the second row. That is, all rows of the elution holes 25 that are disposed along the length of the electrode region may have substantially the same outflow rate. Without a flow constrictor 27, the irrigation system will have an imbalanced outflow pattern where more fluid outflow occurs at the first row. A number of factors are involved in designing an irrigation system with even distribution rate along all of the elution holes. Some of these factors include: size of lumen diameter, percentage differences in diameter decrease, distance between adjacent rows of ducts, diameter of ducts, and tilt angle (if any) of the ducts relative to the main lumen. It is contemplated that the irrigation path described may be modified as dictated by the functional needs of particular applications. For example, in some medical applications more irrigation may be desired in the proximal end and any one or more of the above factors may be adjusted to create an irrigation system to provide more output flow in the proximal region.

In some embodiments, the ducts 24 may have walls with spiral grooves, influencing flow pattern of the fluid flowing through the ducts 24. With such spiral grooves, the fluid comes out of elution holes 24 with an outwardly spraying swirl. This spraying pattern tends to minimize direct impact of the fluid on vessel walls. The spiral grooves can be formed by using an appropriate drill bit. The duct wall can alternatively have other irregular patterns to create other outflow patterns.

In FIG. 7, the flow constrictor 27 is a gradual taper that gradually decreases the main lumen diameter, as opposed to a relatively more abrupt taper seen in FIG. 6. Either abrupt taper or gradual taper, both are preferred over straight angle drop in diameter, because a straight angle drop in diameter can create undesirable eddy currents in the main lumen.

Figure 8:
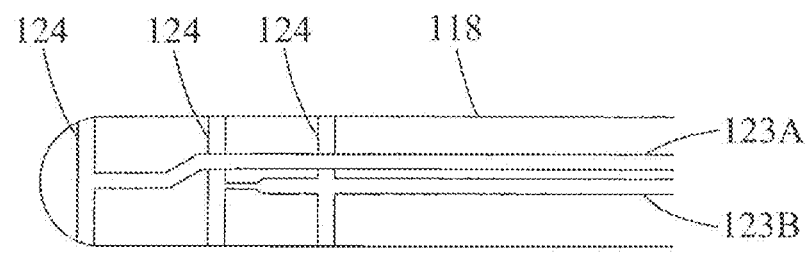
FIG. 8 is a longitudinal cross section view of a catheter distal section illustrating an embodiment having multiple lumens for fluid delivery, according to an aspect of the inventive subject matter.
Figure 9:
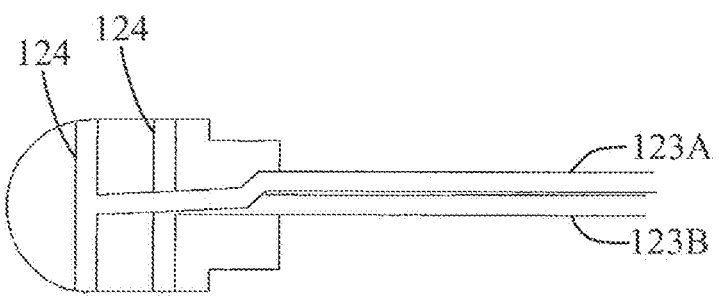
FIG. 9 is a longitudinal cross section view of a catheter distal section illustrating an embodiment having multiple lumens for fluid delivery, according to an aspect of the inventive subject matter.

FIGS. 8 and 9 show yet other embodiments of the present invention. These embodiments have two separate lumens 123A, 123B, with each lumen supplying fluid to corresponding rows of ducts 124. These embodiments are perhaps less desirable because multiple lumens take up precious cross sectional space in catheter body 118. However, it is recognized that even distribution of fluid can be achieved by having separate fluid delivery lumens for separate rows of ducts, with each lumen being precisely pressure and volume flow controlled.

Figure 10:
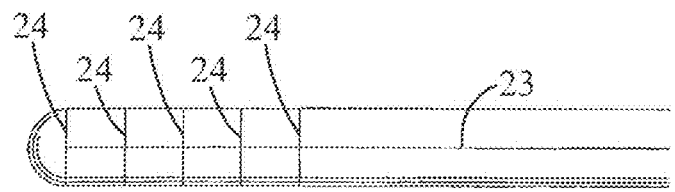
FIG. 10 is a diagrammatic illustration of side channel configuration, according to an aspect of the inventive subject matter.
Figure 11:
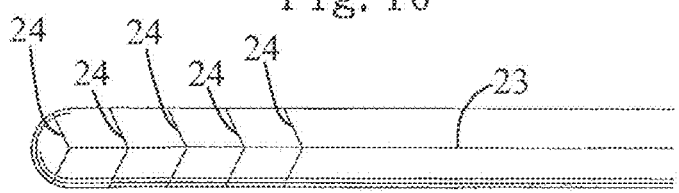
FIG. 11 is a diagrammatic illustration of side channel configuration, according to an aspect of the inventive subject matter.
Figure 12:
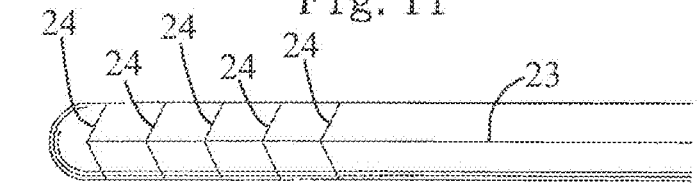
FIG. 12 is a diagrammatic illustration of side channel configuration, according to an aspect of the inventive subject matter.
Figure 13:
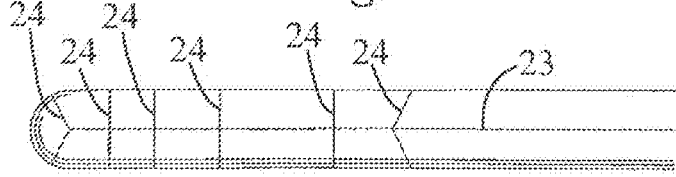
FIG. 13 is a diagrammatic illustration of side channel configuration, according to an aspect of the inventive subject matter.
Figure 14:
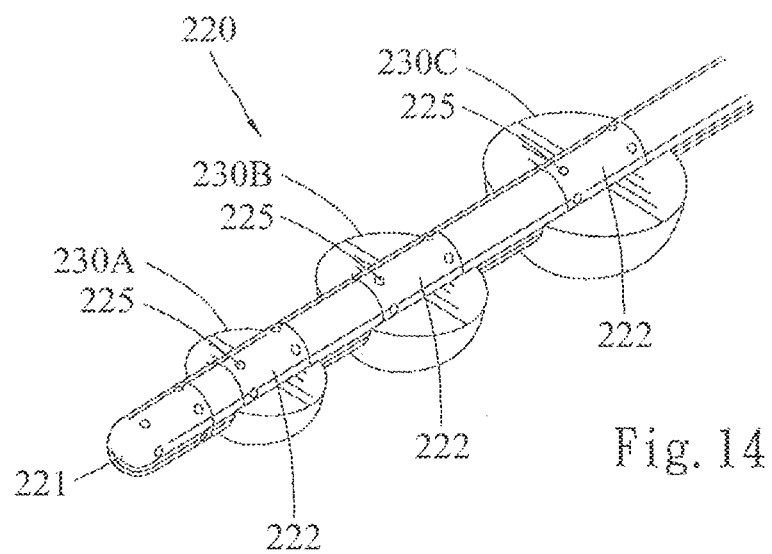
FIG. 14 is a perspective top view of the catheter distal region having inflatable balloons fully inflated, according to an aspect of the inventive subject matter.
Figure 15:
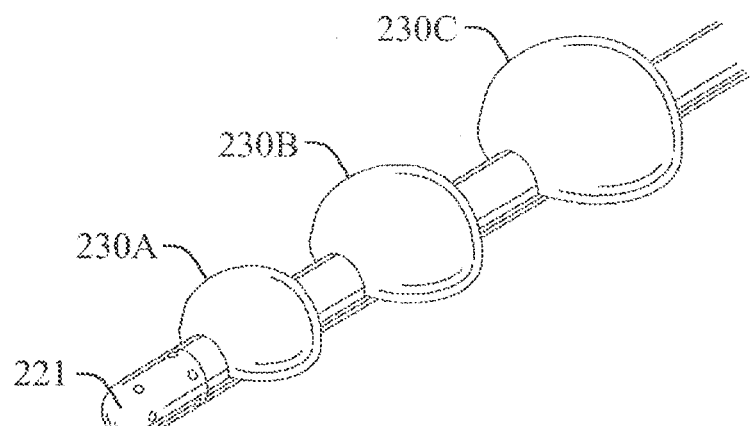
FIG. 15 is a perspective bottom view of the catheter distal region having inflatable balloons fully inflated, according to an aspect of the inventive subject matter.
Figure 16:
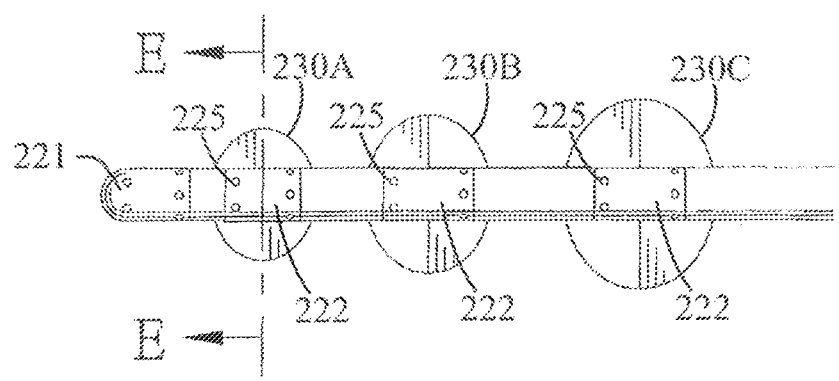
FIG. 16 is a top view of the catheter distal region having inflatable balloons fully inflated, according to an aspect of the inventive subject matter.
Figure 17:
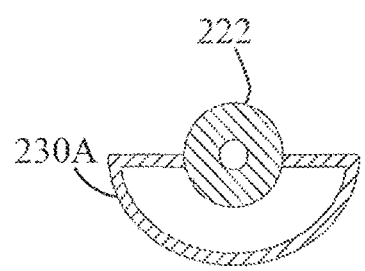
FIG. 17 is a cross sectional view of the catheter distal region of FIG. 16 at line E-E, according to an aspect of the inventive subject matter.

As will be illustrated in connection with FIGS. 10-13, the irrigation system can be advantageously enhanced by arranging the angle of the ducts 24 relative to the main lumen 23. A flow constrictor is omitted from these figures but it is contemplated that a flow constrictor may be required depending on the type of flow output desired. An angle between a longitudinal axis of each of the plurality of ducts 24 and the longitudinal axis of the main lumen may be formed, for example, between 35 to 90 degrees, more specifically, between 45 to 90 degrees and even more specifically between 80 to 90 degrees. In FIG. 10, the ducts 24 are substantially perpendicular to the main lumen 23. In FIG. 11, all of the ducts 24 are tilted towards the distal end, creating a general flow towards the front. In FIG. 12, all of the ducts 24 are tilted towards the proximal end, creating a general flow towards the back. In FIG. 13, a mixture of all three types is provided, creating a general flow away from the ablation area.

In FIGS. 14-17, three inflatable balloons 230A, 230B, 230C can be optionally provided to the electrode catheter as discussed above. Alternatively, this can be a balloon catheter with optional electrodes for ablation. The balloons 230 help navigate and position the electrode 222 to the targeted ablation site. As discussed earlier, elution holes 225 may be provided for irrigation purposes, and the catheter has a catheter tip 221. The catheter is first inserted into the patient while the balloon 230 is deflated. Once the user finds the targeted ablation location, the balloon 230 inflates, pushing the electrode side 222 of the catheter region against or closer to the ablation area. As opposed to electrodes described above, these embodiments have electrodes 222 on only the top side of the catheter distal portion. The underside has inflatable balloons 230.

Contemplated devices may have just a single balloon 230, or a plurality of balloons 230. Where a plurality of balloons 230 are provided, the balloons can be of the same size and shape, or alternatively, each balloon 230 can have a distinct shape and size. An exemplary embodiment includes three balloons 230A, 230B, 230C, with the smallest one at the distal end, and the largest one on the proximal end. This configuration facilitates manipulation of the catheter in a funnel-shaped vessel. When a funnel-shaped vessel closely corresponding to shape of the balloons catheter distal region when inflated, the balloon catheter in FIGS. 14-17 can more fittingly secure itself and position the electrode at the ablation region. Exemplary balloons may be half-dome shaped, and may have a cross sectional shape resembling a half circle. Also contemplated is a configuration having at least one inflatable balloon, where at least one balloon has an inflated shaped that resembles a longitudinally dissected cone, or half-cone. By providing one balloon, or a plurality of balloons, an overall general shape that corresponds to a funnel-shaped vessel may be provided. This overall general shape can be a longitudinally dissected cone shape, a longitudinally dissected oval (egg-like) shape where a distal end is smaller than the proximal end, or any other shapes where the cross-sectional area is smaller at the distal portion of the overall shape than at its proximal portion. The device may use typical controlling parts and other related configuration for using and positioning the balloon 230, such as those disclosed in U.S. Pat. Nos. 7,137,395 and 6,780,183.

Balloon catheter devices are well known and general features (e.g. size, shape, materials) of the balloons 230 may be in accordance with conventional balloons. In one embodiment, the balloons 230 may be made of flexible medical-grade silicone rubber. Alternatively, the balloon 230 may be made of other biocompatible and distendable materials, such as polyethylene terephthalate (PET).

While the various embodiments of the irrigation system is herein disclosed as suitable for ablation catheters that perform tissue ablation, and the fluid being suitable cooling fluid such as saline, the same uniform distribution concept can be applied to drug delivery catheters desiring to delivery therapeutic fluid at a uniform rate among the many delivery bores on the catheter distal region.

Thus, specific embodiments and applications of irrigated catheters have been disclosed. It should be apparent, however, to those skilled in the art that many more modifications besides those already described are possible without departing from the inventive concepts herein. The inventive subject matter, therefore, is not to be restricted except in the spirit of the appended claims.

The invention claimed is:

1. A catheter comprising:
   a distal end;
   a proximal end;
   a longitudinal axis;
   a lumen that includes a first segment having a first inner diameter and a second segment having a second inner diameter that is different from the first inner diameter;
   an electrode coupled to the distal end and having a terminal end;
   a sidewall defining a plurality of elution openings including a first elution opening and a second elution opening longitudinally spaced apart from the first elution opening, each of the first elution opening and the second elution opening spaced from the terminal end and extending into the sidewall, wherein the plurality of elution openings are proximal of said terminal end; and
   a plurality of ducts including a first duct and a second duct, the first duct extending at a first angle with respect to the longitudinal axis and between the first segment and the first elution opening, the second duct extending at the first angle with respect to the longitudinal axis and between the second segment and the second elution opening.

2. The catheter of claim 1, wherein the first inner diameter is greater than the second inner diameter and the second segment is distal to the first segment.

3. The catheter of claim 1, wherein the first inner diameter of the lumen is tapered and is reduced in size towards the distal end of the catheter.

4. The catheter of claim 1, further comprising at least one additional electrode coupled to the catheter, and at least one additional elution opening provided in the at least one additional electrode.

5. The catheter of claim 1, wherein a longitudinal axis of each of the plurality of ducts and the cathteter longitudinal axis are at a respective angle between about 35 to about 90 degrees.

6. The catheter of claim 1, wherein an inner diameter of the lumen varies from about 0.005 inches to about 0.045 inches, and wherein the first inner diameter is decreased by about 5% to about 40% along a longitudinal length of the catheter toward the distal end.

7. The catheter of claim 1, wherein a longitudinal axis of at least one of the plurality of ducts is oblique with respect to the catheter longitudinal axis.

8. The catheter of claim 7, wherein a length of the at least one of the plurality of ducts is inclined to define a fluid path extending forwardly or rearwardly from the lumen to an elution opening.

9. The catheter of claim 1, wherein the electrode comprises the first segment and the second segment.

10. The catheter of claim 1, wherein the electrode comprises the sidewall.

11. An irrigated electrode catheter comprising:
    a longitudinal axis;
    a sidewall;
    a distal region having a fluid delivery lumen defined by an inner surface of the sidewall, the lumen including a first segment having a first inner diameter and a second segment having a second inner diameter that is about 5% to about 40% smaller than the first inner diameter; and
    at least one electrode at the distal region and including a plurality of longitudinally spaced apart ducts including a first duct and a second duct, the first duct extending at a first angle with respect to the longitudinal axis and from the first segment to the sidewall, the second duct extending at the first angle with respect to the longitudinal axis and from the second segment to the sidewall.

12. The irrigated electrode catheter of claim 11, wherein a first set of the plurality of longitudinally spaced apart ducts extends from the first segment and a second set of the plurality of longitudinally spaced apart ducts extends from the second segment, each of the first set of ducts and the second set of ducts being distributed circumferentially about the lumen.

13. The irrigated electrode catheter of claim 11, wherein the ducts have an irregular surface pattern that defines a spiral groove, and wherein a flow pattern comprises an outwardly spraying swirl.

14. The catheter of claim 11, wherein each of the plurality of ducts include an inner diameter being approximately equal among the plurality of ducts.

15. The catheter of claim 11, wherein the at least one electrode further comprises a plurality of first elution openings and a plurality of second elution openings, the first elution openings having coplanar centers, the second elution openings having coplanar centers.

16. The catheter of claim 11, wherein the first elution openings are evenly spaced circumferentially and the second elution openings are evenly spaced circumferentially, and wherein the first elution openings are rotationally offset from the second elution openings by an angle.

17. The irrigated electrode catheter of claim 11, wherein the at least one electrode comprises the first segment and the second segment.

* * * * *